US00PP34262P2

(12) United States Plant Patent
Bradford et al.

(10) Patent No.: US PP34,262 P2
(45) Date of Patent: May 24, 2022

(54) NECTARINE TREE NAMED 'PEARLICIOUS IV'

(50) Latin Name: *Prunus persica*
Varietal Denomination: Pealicious IV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,913

(22) Filed: Dec. 17, 2021

(51) Int. Cl.
*A01H 5/08* (2018.01)
*A01H 6/74* (2018.01)

(52) U.S. Cl.
USPC ..... Plt./188

(58) Field of Classification Search
USPC ..... Plt./187, 188
See application file for complete search history.

(56) References Cited

U.S. PATENT DOCUMENTS

PP18,715 P2 4/2008 Bradford
PP22,758 P2 5/2012 Bradford

*Primary Examiner* — Susan McCormick Ewoldt

(57) ABSTRACT

The present invention relates to a new and distinct variety of nectarine tree, *Prunus persica*, broadly characterized by a small to medium size, moderately vigorous, hardy, self-fertile, productive and regular bearing tree. The variety blooms just before mid season and requires about 500 chilling hours. The fruit matures under the ecological conditions described in the last week of May, with first picking on May 23, 2021. The fruit is uniform, medium to large in size, globose to oblate in shape, semi-freestone in type, firm in texture, sub-acidic and very sweet in flavor, white in flesh color, almost full red in skin color, and has a bitter tasting kernel.

1 Drawing Sheet

Botanical classification: *Prunus persica.*
Variety denomination: 'PEARLICIOUS IV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious IV'.

In 2013 we made a first generation hybridization using 'Kay Diamond VII' (U.S. Plant Pat. No. 18,715) nectarine as the selected seed parent and '8P1239' (unpatented) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2017 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Kay Diamond VII' (U.S. Plant Pat. No. 18,715) nectarine, by being self-fertile and by producing nectarines that ripen in the early season and that are nearly full red in skin color, medium to large in size and firm in texture, but is quite distinguished from it by having globose leaf glands instead of being eglandular and by producing fruit that is white instead of yellow in flesh color, that is much sweeter, and that is sub-acidic instead of acidic in flavor.

The present variety is similar to its pollen parent, '8P1239' (unpatented) nectarine, by being self-fertile and by producing nectarines that are mostly red in skin color, white in flesh color, and sub-acidic in flavor, but is quite distinguished from it by producing fruit that is larger in size, that is much sweeter in flavor, and that ripens about five days earlier.

The present variety is most similar to 'Pearlicious I' (U.S. Plant Pat. No. 22,758) nectarine by being self-fertile, by having a large blossom and by producing nectarines that are white in flesh color, that are almost full red in skin color, that are firm in texture, and that are sweet and sub-acidic in flavor, but is distinguished therefrom by blooming later, requiring more chilling hours, and having globose instead of reniform leaf glands and by producing nectarines that are slightly larger in size, that are semi-freestone instead of clingstone in type, that have a bitter instead of sweet kernel, and that mature about three days earlier.

SUMMARY OF VARIETY

In summary, the present nectarine variety is characterized by a small to medium size, moderately vigorous, hardy, self-fertile, productive and regular bearing tree. The variety blooms just before mid season and requires about 500 chilling hours. The fruit matures under the ecological conditions described in the last week of May, with first picking on May 23, 2021. The fruit is uniform, medium to large in size, globose to oblate in shape, semi-freestone in type, firm in texture, sub- acidic and very sweet in flavor, white in flesh color, almost full red in skin color, and has a bitter tasting kernel.

DRAWING

The accompanying photograph consists of four whole fruits positioned to display the characteristics of the skin color and form, one divided fruit to reveal the flesh and stone, typical leaves, an isolated stone, a tip shoot of new leaf growth and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on May 29, 2021, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: 'Kay Diamond VII' (U.S. Plant Pat. No. 18,715) nectarine.
Pollen parent: '8P1239' (unpatented) nectarine.

TREE

Size: Small to medium, reaching and maintaining a height of 9' [2.74 m.] and a spread of 9' [2.74 m.] after eight growing seasons utilizing typical dormant pruning.
Vigor: Moderately vigorous, responding about average to irrigation and fertilization. The variety grows about 2' [0.61 m.] of surplus top-growth during the spring and summer. The plant should be grown on a standard commercial rootstock for production purposes.
Growth: Spreading and open.
Form: Pruned to a vase shape.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-fertile.
Bearing: Regular bearer, with no crop failures observed.
Chilling requirement: About 500 hours.
Leaf bud burst: Medium to late, during the end of flowering.
Trunk:
- *Size*.—Stocky to medium, reaching a maximum diameter of 4¾" [120.7 mm.] after the eighth growing season.
- *Texture*.—Medium to shaggy.
- *Bark color*.—A Light brownish gray [63. l.brGy] and Light grayish brown [60. l.gy.Br] variegation with Moderate brown [58. m.Br] crevices present.
- *Lenticels*.—Approximate Number Per Square Inch: 12. Color: Deep orange yellow [69. deep OY]. Average Size: ⅜" [9.5 mm.] in length. The width is typically one fourth as much as the length. Shape: Elongated.

Branches:
- *Size*.—Medium to slender, diameter of main scaffold is 3" [76.2 mm.] measured 12" above the crotch, diameter of limb is 1½" [38.1 mm.] measured 12" above the first fork.
- *Texture*.—Smooth to medium on first and second year wood, increasing in roughness with age.
- *Color*.—1st Year Wood Topside: Grayish red [19. gy.R]. 1st Year Wood Underside: Brilliant yellow green [116. brill.YG]. Older Wood: A Light grayish yellowish brown [79. l.gy.yBr] and Moderate yellowish brown [77. m.yBr] variegation with Dark yellowish brown [78. d.yBr] crevices present.
- *Lenticels*.—Number Per Square Inch: About 30 on second year wood. Color: Strong yellowish brown [74. s.yBr]. Average Size: Small, 1/16" [1.6 mm.] in length. The width is typically one fourth as much as the length. Shape: Elongated.

Leaves:
- *Size*.—Large. Average Length: 6½" [165.1 mm.]. Average Width: 1¾" [44.5 mm.].
- *Arrangement*.—Alternate.
- *Thickness*.—Medium.
- *Form*.—Elliptical.
- *Apex*.—Acuminate.
- *Base*.—Acute, with an average base angle of 75 degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: 5/16" [7.9 mm.]. Average Thickness: 1/16" [1.6 mm.]. Color: Strong yellow green [117. s.YG].
- *Stipules*.—Number: 2 per leaf, up to 6 per growing tip. Average Length: ¼" [6.4 mm.]. Color: Vivid yellow green [115. v.YG] becoming Moderate brown [58. m.Br] with age.
- *Glands*.—Number: 2 to 4 per leaf. Position: Alternate, first pair is located at the intersection of petiole and base of blade. Form: Globose. Size: Small to medium, about 1/32" [0.8 mm.] in diameter. Color: Light yellow green [119. l.YG] becoming Dark olive brown [96. d.OlBr] with age.
- *Leaf buds*.—Pointed.

Flower buds:
- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.

*Form*.—Not appressed.
*Surface*.—Pubescent.
*Tip color*.—Pale purplish pink [252. p.pPk].

Flowers: Perfect, complete, perigynous, usually a single pistil, about thirty stamens, five sepal and petal locations alternately positioned.
*Type*.—Showy, large.
*Average flower diameter*.—2" [50.8 mm.].
*Average flower depth*.—½" [12.7 mm.] when fully open.
*Number of petals*.—Five, extra petal fragments occur frequently, double blossoms occasionally observed.
*Petal arrangement*.—Overlapping.
*Petal shape*.—Circular to oval.
*Petal margin*.—Entire, slightly wavy.
*Average petal diameter*.—13/16" [20.6 mm.].
*Average petal length*.—⅞" [22.2 mm.].
*Petal apex*.—Rounded.
*Petal base*.—Rounded to slightly obtuse.
*Petal color*.—Light pink [4. l.Pk] toward the apex and Moderate pink [5. m.Pk] toward the base on both sides.
*Anthocyanin coloration intensity*.—Weak.
*Anther color*.—Strong reddish orange [35. s.rO] surrounding a Brilliant yellow [83. brill.Y] center at bloom onset.
*Pollen*.—Anthers produce an abundance of Brilliant yellow [83. brill.Y] pollen.
*Stigma color*.—Brilliant greenish yellow [98. brill.gY].
*Stigma position*.—Typically located about ⅛" [3.2 mm.] above the nearby anthers.
*Stamen position*.—Typically located about 1/16" [1.6 mm.] below the petal bases.
*Average pistil length*.—13/16" [20.6 mm.].
*Average stamen length*.—½" [12.7 mm.].
*Ovary*.—Non-pubescent.
*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—⅜" [9.5 mm.].
*Sepal width*.—5/16" [7.9 mm.].
*Sepal apex*.—Rounded to elliptical to match the sepal length and width.
*Sepal margin*.—Fairly smooth.
*Sepal outer surface*.—Pubescent.
*Fragrance*.—Moderate.
*Blooming period*.—Just before mid season, blooms about three days before 'Majestic Pearl' (U.S. Plant Pat. No. 18,778) nectarine.
*Onset of bloom*.—One percent on Feb. 15, 2021.
*Date of full bloom*.—Feb. 26, 2021.
*Duration of bloom*.—One to two weeks, dependent on ambient temperature.
*Bloom density*.—Medium to heavy.
*Number per cluster*.—1 to 3 with single flowers most common.

FRUIT

Maturity when described: Firm ripe, May 29, 2021.
Date of first picking: May 23, 2021.
Date of last picking: Jun. 7, 2021.
Size: Uniform, medium to large.
*Average diameter axially*.—2⅞" [63.5 mm.].
*Average diameter across suture plane*.—3" [76.2 mm.].
*Average diameter across cheek plane*.—2 15/16" [74.6 mm.].
*Typical weight*.—7.7 ounces [218 grams].

Form: Uniform, globose to slightly oblate, symmetrical.
*Longitudinal section form*.—Round to slightly oblate.
*Axial view*.—Round.

Suture: A shallow trough extending from the base, along the side, and becoming a shallow groove that terminates about ½" [12.7 mm.] beyond the pistil point.
*Near the base*.—A very shallow trough.
*Along the side*.—A very shallow trough.
*Near the apex*.—A shallow groove.

Ventral surface: Rounded, lipped on both sides.
Lips: Fairly equal.
Cavity: Flaring, with Pale greenish yellow [104. p.gY] stem markings present.
*Depth*.—7/16" [11.1 mm.].
*Breadth*.—1⅜" [34.9 mm.].
Base: Rounded to slightly truncate.
Apex: Rounded to slightly truncate, cordate when viewed parallel to the suture.
Pistil point: Apical, negligible in length, depressed within the suture.
Stem: Medium.
*Average length*.—⅜" [9.5 mm.].
*Average width*.—3/16" [4.8 mm.].

Skin:
*Thickness*.—Medium.
*Surface*.—Smooth.
*Tenacity*.—Tenacious to the flesh.
*Astringency*.—Non-astringent.
*Tendency to crack*.—None observed.
*Color*.—Very dark red [17. v.d.R] blending into a Strong red [12. s.R] background with moderate Light yellow [86. l.Y] freckling toward the apex.

Flesh:
*Color*.—Greenish white [153. gWhite] with a very small amount of Moderate red [15. m.R] flecking between the stone and skin.
*Surface of pit cavity*.—Covered with Greenish white [153. gWhite] broken fibers when twisted away from the stone.
*Amygdalin*.—Scarce.
*Juice*.—Moderate, rich.
*Texture*.—Firm, crisp, meaty.
*Fibers*.—Abundant, fine, tender.
*Ripens*.—Fairly even.
*Flavor*.—Sub-acidic, very sweet, typically 19 brix.
*Aroma*.—Very slight.
*Eating quality*.—Excellent.

STONE

Type: Semi-freestone.
Form: Oval to globose.
Hilum: Narrow, oval.
Base: Rounded.
Apex: Rounded with a needle-like tip protruding.
Sides: Equal.
Tip: Very sharp, 1/16" [1.6 mm.] in length.
Surface: Irregularly furrowed toward the apex, pitted toward the base.
Ridges: Jagged.

External color: Light brown [57. l.Br] when first removed.
Pit wall color when cracked: Light yellowish brown [76. l.yBr].
Cavity surface color: A Light yellowish brown [76. l.yBr] and Deep yellowish brown [75. deep yBr] mixture.
Average pit wall thickness: 3/16" [4.8 mm.].
Average length: 1 1/8" [28.6 mm.].
Average width: 1 1/16" [27.0 mm.].
Average breadth: 3/4" [19.1 mm.].
Tendency to split: None observed.
Kernel:

*Form*.—Oval.
*Skin color*.—Pale yellow [89. p.Y].
*Pellicle color*.—Deep yellowish brown [75. deep yBr].
*Vein color*.—Light yellow [86. l.Y].
*Taste*.—Slightly bitter.
*Viable*.—Yes.
*Average length*.—9/16" [14.3 mm.].
*Average width*.—7/16" [11.1 mm.].
*Amygdalin*.—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, California, in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Pearlicious I' (U.S. Plant Pat. No. 22,758) nectarine by being self-fertile, by having a large blossom and by producing nectarines that are white in flesh color, that are almost full red in skin color, that are firm in texture, and that are sweet and sub-acidic in flavor, but is distinguished therefrom by blooming later, requiring more chilling hours, and having globose instead of reniform leaf glands and by producing nectarines that are slightly larger in size, that are semi-freestone instead of clingstone in type, that have a bitter instead of sweet kernel, and that mature about three days earlier.

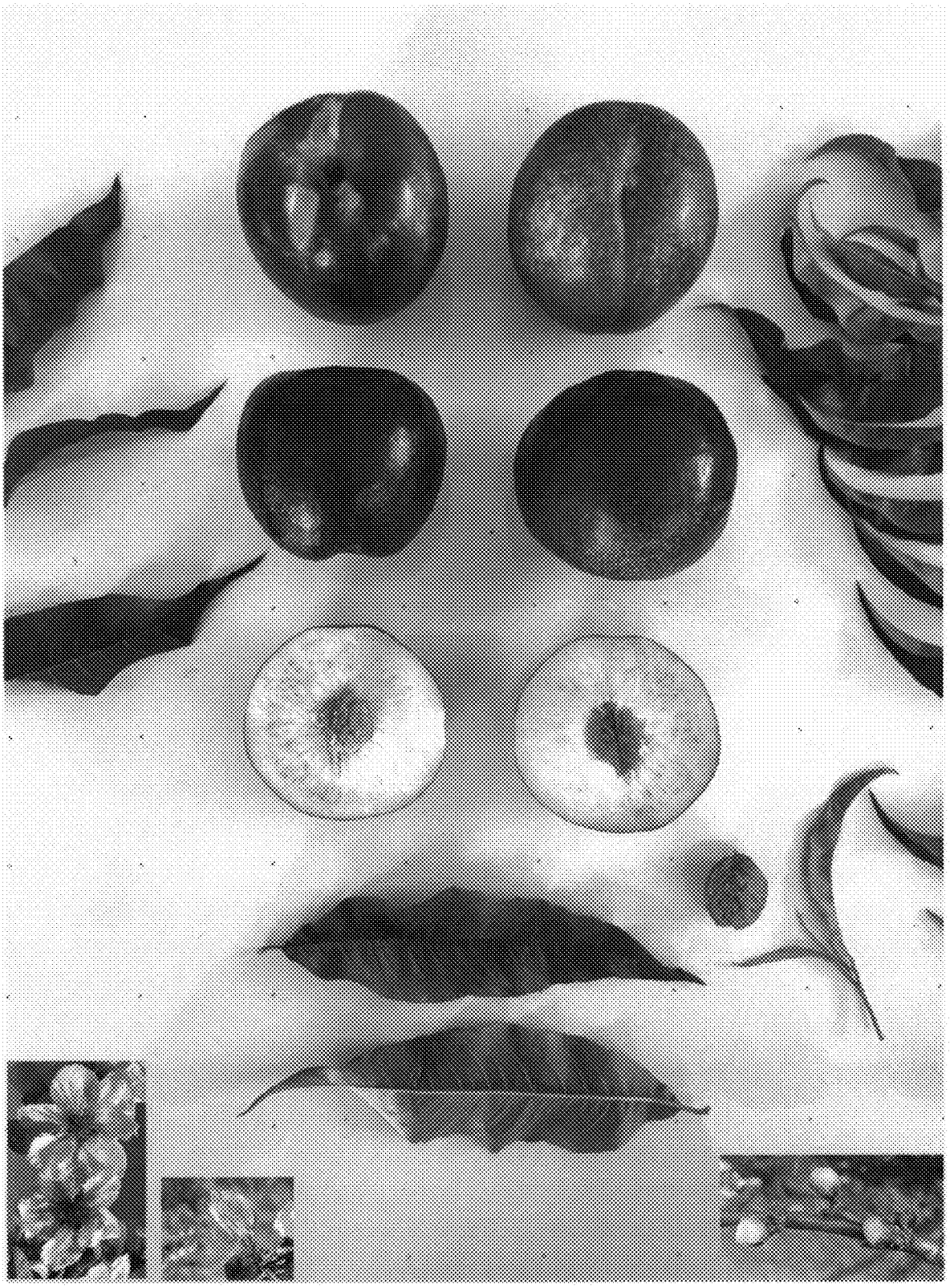

* * * * *